(12) United States Patent
Tremolada

(10) Patent No.: US 9,192,939 B2
(45) Date of Patent: Nov. 24, 2015

(54) DEVICE AND A METHOD FOR PREPARING A TISSUE

(75) Inventor: Carlo Tremolada, Milan (IT)

(73) Assignee: LIPOGEMS INTERNATIONAL S.P.A., Milan (IT)

( * ) Notice: Subject to any disclaimer, the term of this patent is extended or adjusted under 35 U.S.C. 154(b) by 388 days.

(21) Appl. No.: 13/636,572

(22) PCT Filed: Mar. 22, 2011

(86) PCT No.: PCT/IB2011/051206
§ 371 (c)(1),
(2), (4) Date: Oct. 31, 2012

(87) PCT Pub. No.: WO2011/117821
PCT Pub. Date: Sep. 29, 2011

(65) Prior Publication Data
US 2013/0087643 A1    Apr. 11, 2013

(30) Foreign Application Priority Data

Mar. 23, 2010  (IT) .............................. GE2010A0026
Mar. 23, 2010  (IT) .............................. GE2010A0028

(51) Int. Cl.
*B02C 23/00*   (2006.01)
*A61K 35/35*   (2015.01)
*C12M 1/33*    (2006.01)

(52) U.S. Cl.
CPC ................ *B02C 23/00* (2013.01); *A61K 35/35* (2013.01); *C12M 45/02* (2013.01)

(58) Field of Classification Search
CPC .............................. C12M 45/02; A61K 35/35
USPC ....................................... 241/2, 169.1, 95, 60
See application file for complete search history.

(56) References Cited

U.S. PATENT DOCUMENTS 3,941,317 A   3/1976   Kanor
6,020,196 A   2/2000   Hu

FOREIGN PATENT DOCUMENTS

JP    2009038998    2/2009

*Primary Examiner* — Mark Rosenbaum
(74) *Attorney, Agent, or Firm* — Themis Law

(57) ABSTRACT

A device and a method for preparing adipose tissue for transplantation from lobular fat material extracted by liposuction, the fat material consisting of a mixture of fluid materials and cell fragments, cells and one or more cell magroagglomerates of heterogeneous sizes, include at least one sterile container having a size reducing device for reducing the fat material into cell agglomerates of smaller and identical or similar sizes, the device dividing the inner chamber of the container into at least two portions, particularly a first upper portion and a second lower portion.

9 Claims, 7 Drawing Sheets

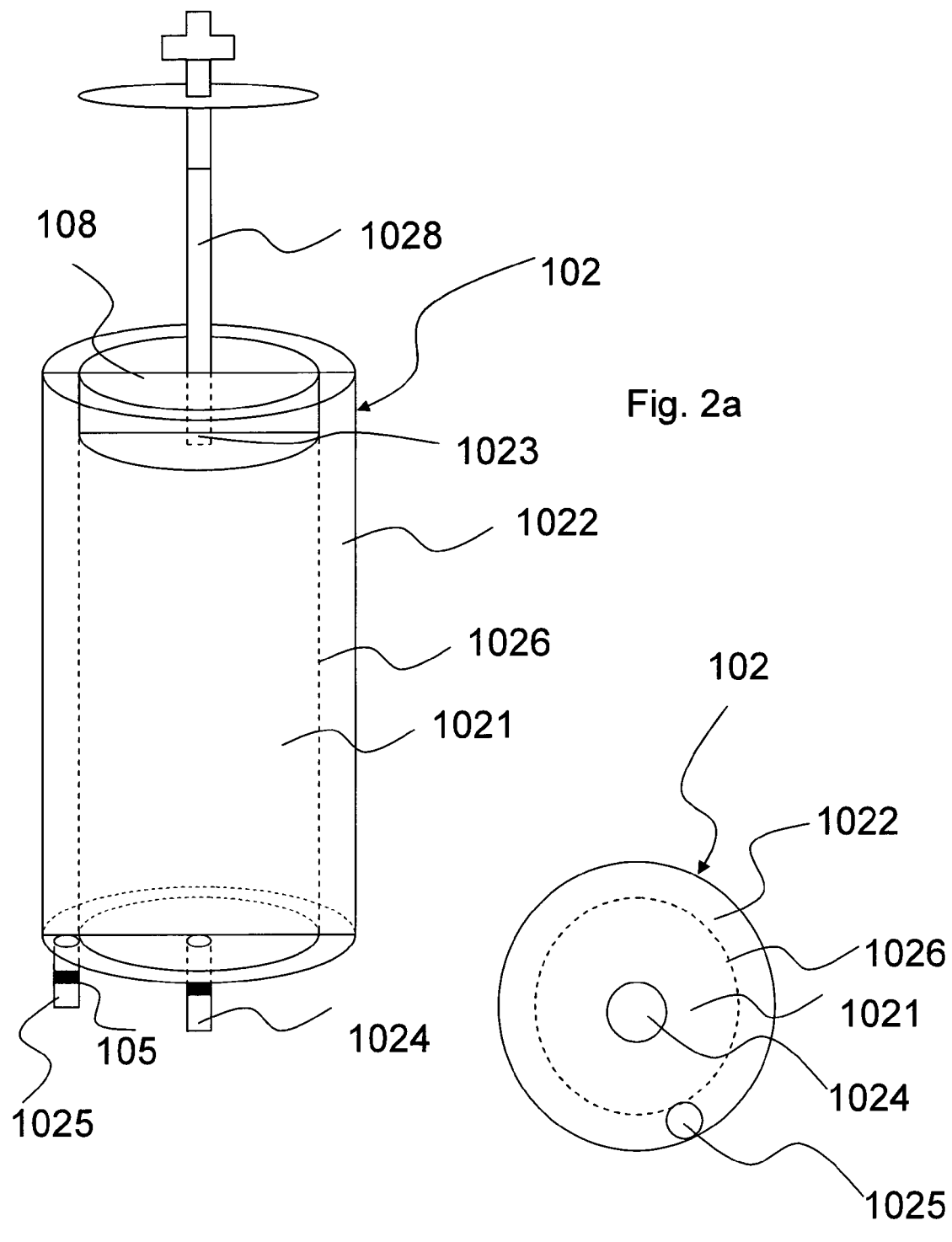

DEVICE AND A METHOD FOR PREPARING A TISSUE

Figure 1:
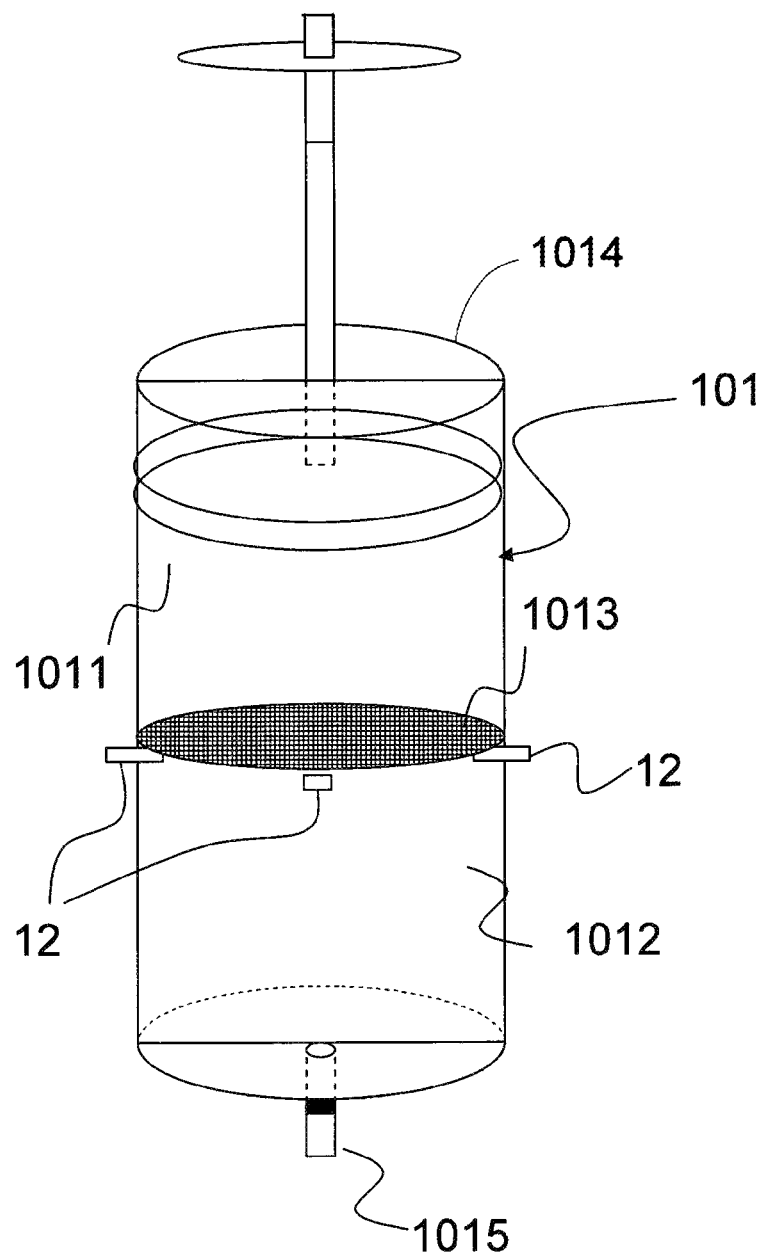

The present invention relates to a device and a method for preparing tissue, particularly adipose tissue, for transplantation from lobular fat extracted by liposuction.

Prior art techniques are disclosed in U.S. Pat. No. 6,020, 196 and U.S. Pat. No. 3,941,317.

Lobular fat, i.e. the fat composed of macroagglomerates of adipose cells yielded by liposuction, is known to be transformed into a biological filler, i.e. a cell suspension composed of adipocytes, stem cells and connective material, which suspension may be injected for volume correction in the face and body and for improvement of skin trophism even in the presence of pathological conditions, such as scars, ulcers and radiodermatitis.

According to the prior art, the preparation required to reuse the liposuctioned material involves the separation of the vital cell component to be reinjected from the waste material composed of anesthetic liquid or biological fluids (serum or blood) and cell debris and oil resulting from the rupture of suctioned adipocytes.

The object of the present invention is to provide a device for preparing tissue for transplantation from lobular fat, i.e. fat composed of cell macroagglomerates, cells and cell fragments, obtained by means of liposuction, that may obviate the above drawbacks.

A further object of the present invention is a method that involves the use of said device for preparing tissue, particularly adipose tissue for transplantation.

Particularly, the device of the present invention allows preparation of cell agglomerates, particularly adipocyte agglomerates, using a few simple instruments and through a few processing steps, to completely eliminate the oily component and avoid handling of the biological material as much as possible. Thus, also due to the use of specially thin needles, the transplantation of adipose tissue will be less invasive, less traumatic and more effective. Therefore, the cell agglomerates yielded by the device of the present invention are prepared with minimized contact with the atmosphere and using disposable instruments that reduce the risks of contamination of the biological material, the risks of instrument deterioration and the drawbacks associated with washing and re-sterilization. The biological material so obtained may be injected into any tissue or organ.

The above objects are obtained using a device as defined hereinafter. The size reducing means of described herein may be provided in various different embodiments.

As is apparent from the following description of preferred embodiments, fat passes through the various portions of the container that form the device of the present invention by application of a given pressure on the content of said containers, i.e. on the fat to be treated, by using compression means such as syringes connected to said containers, plungers cooperating with said containers or the like.

Therefore, in a first step, the device allows adipose tissue extracted by liposuction, said fat consisting of a mixture of fluid substances and cell fragments, cells and one or more cell macroagglomerates of heterogeneous sizes, to be divided into cell agglomerates smaller than said macroagglomerates, so that said cell agglomerates are as large as or smaller than a predetermined size, and so that they are on average of the same size.

Thus, a suspension or a cell mass is obtained, containing cell fragments, individual cells and agglomerates of cells, particularly adipocytes and stem cells of small and on average similar sizes.

In a later step, the device allows washing and separation of said cell mass from the mixture of fluid materials, such as saline, anesthetic solution, blood and oil, so that a minimized amount of undesired impurities are collected at the end of the procedure with the cells or cell aggregates, particularly adipocytes.

The transformation of lobules of adipose tissue yielded by liposuction into a biological filler, i.e. a cell suspension or mass or a fluid or semifluid agglomerate containing adipocytes, other types of cells, such as stem or mesenchymal cells, and possibly cell fragments and residues of connective material, which suspension, at the end of the transformation procedure of the present application, has a solid phase composed of cells and/or cell aggregates of small, averagely homogeneous sizes, adapted to be injected in small or large amounts, allows the prepared fat to be used not only in an intra- or submuscular injection, but also in subcutaneous injections, without irregularities, hardening effects, calcifications and total reabsorption of the injected fat.

Nevertheless, the fat material may be injected into any tissue or organ.

The very small sizes of the cell agglomerates obtained by the above device allow the use of transplantation cannulae of particularly small size, which will reduce the trauma caused by the transplantation procedure, and allow the latter to be performed under local anesthesia, with no suture or particular medication and with fast healing results.

Furthermore, the separation of fat lobules into small cells or cell agglomerates facilitates engraftment, i.e. integration of the cell mass in the tissues in which it is injected.

The division of fat lobules into cell aggregates provides both the advantage of allowing the use of very small transplantation cannulae and that of increasing the surface of the injected cell mass that contacts the tissues undergoing transplantation, thereby promoting biological stimulation of treated tissues and hence integration of the injected cell material.

The use of a simple device, composed of a few sterile components, which isolate the extracted biological material from the external environment actually throughout the preparation procedure, considerably reduces the risk of contamination of the biological material, the personnel and the environment, and hence the risk of infections or rejections during later use of the cell material.

Therefore, the device of the present invention also allows treatment of biological material outside operating rooms, in outpatient settings.

Figure 1A:
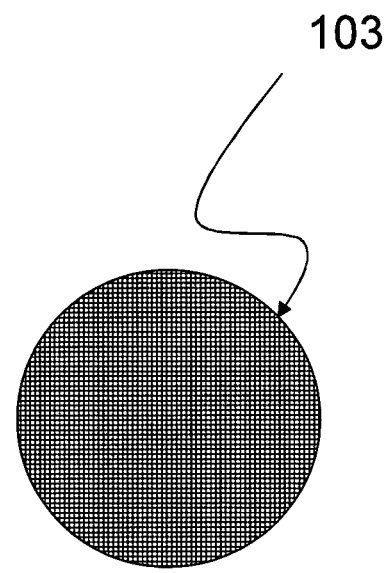
Figure 1B:
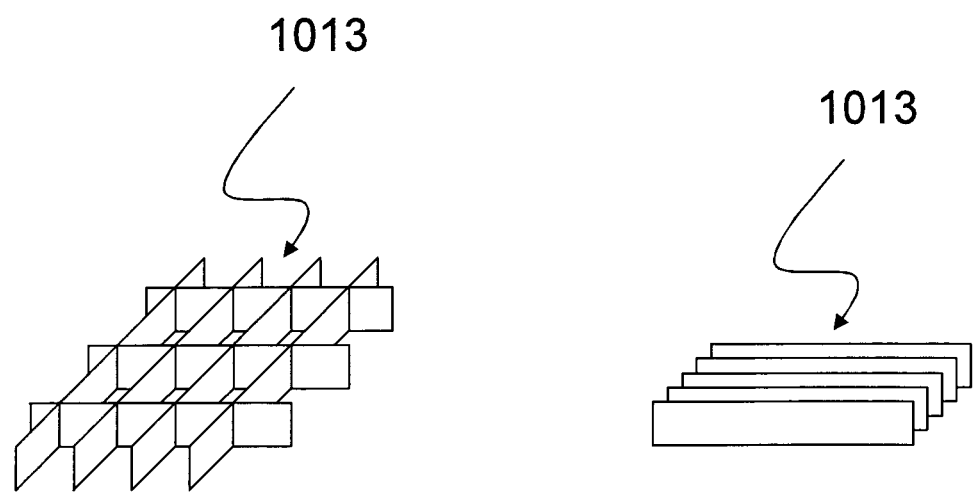
Figure 1C:
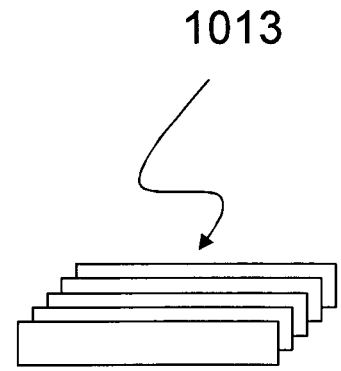
Figure 3:
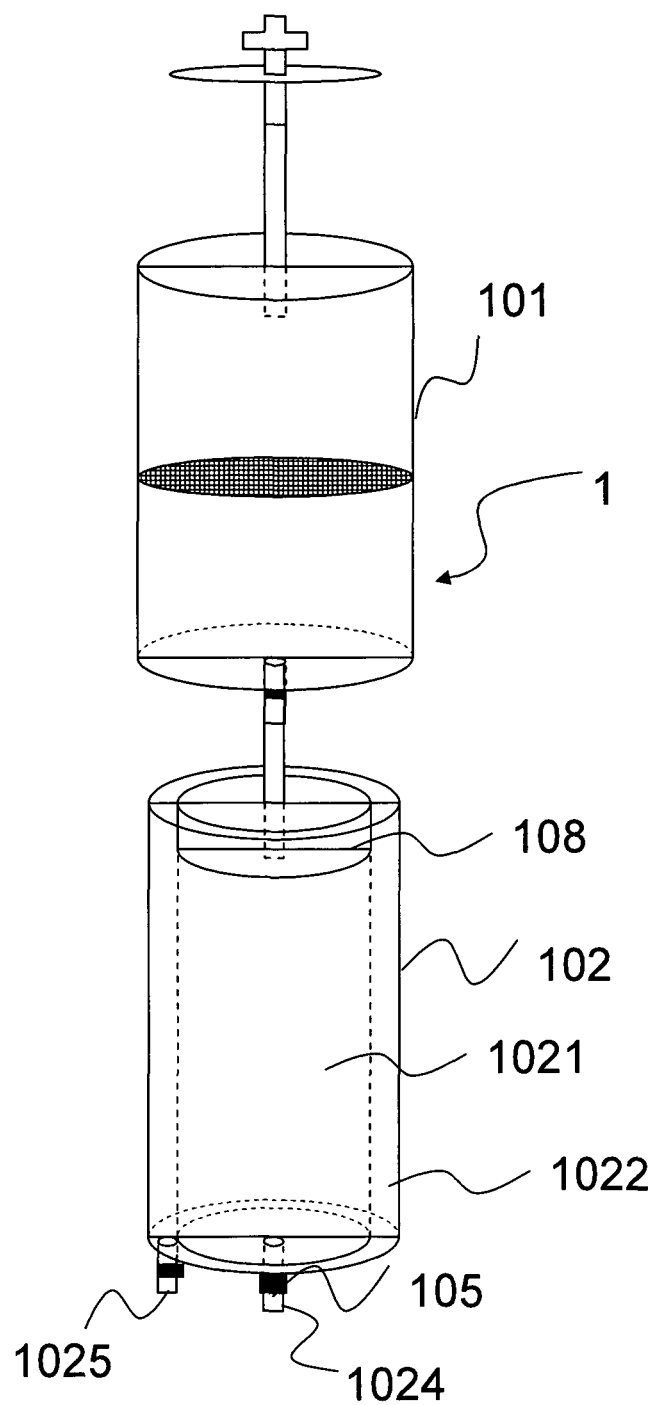
Figure 4:
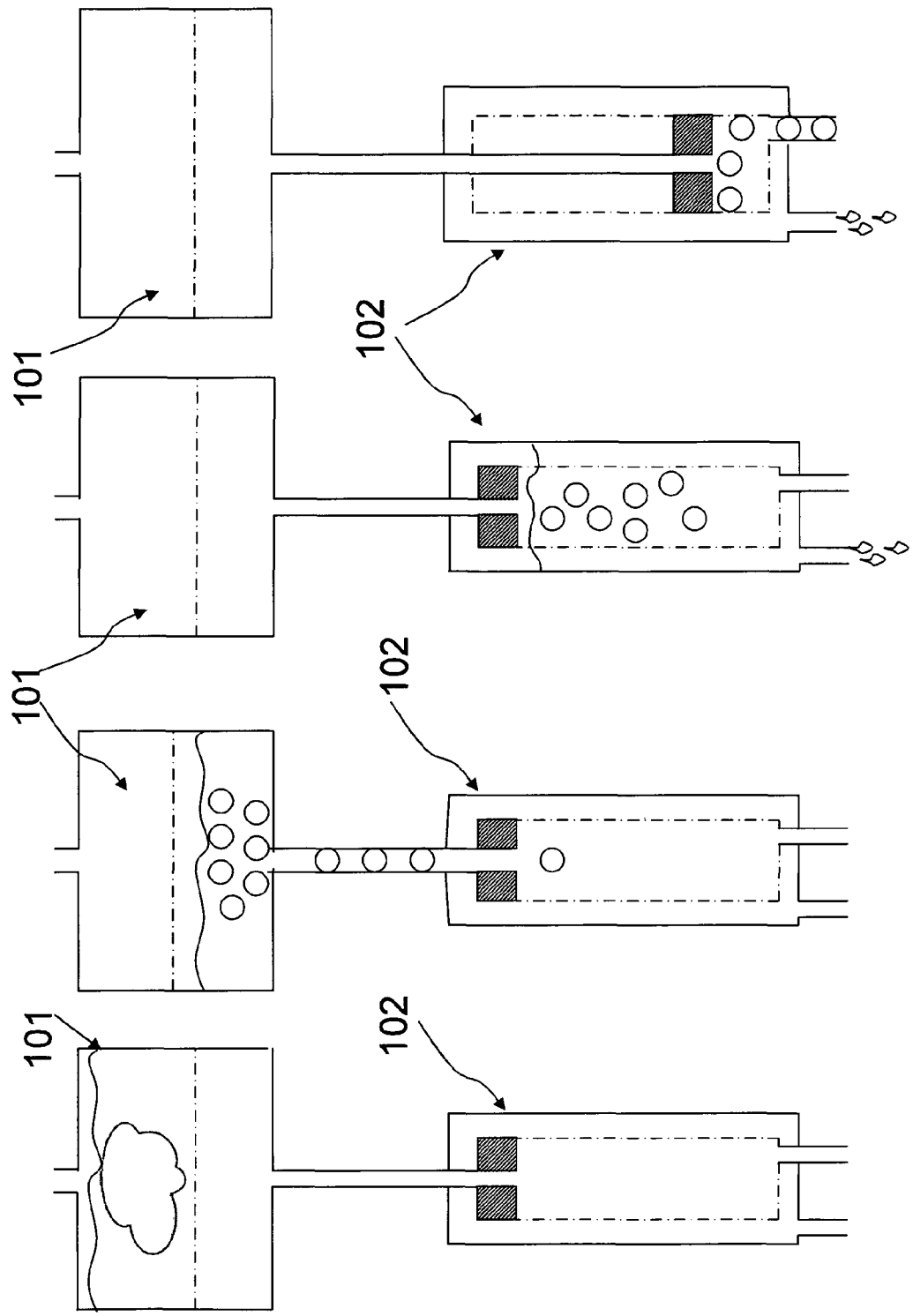
Figure 5:
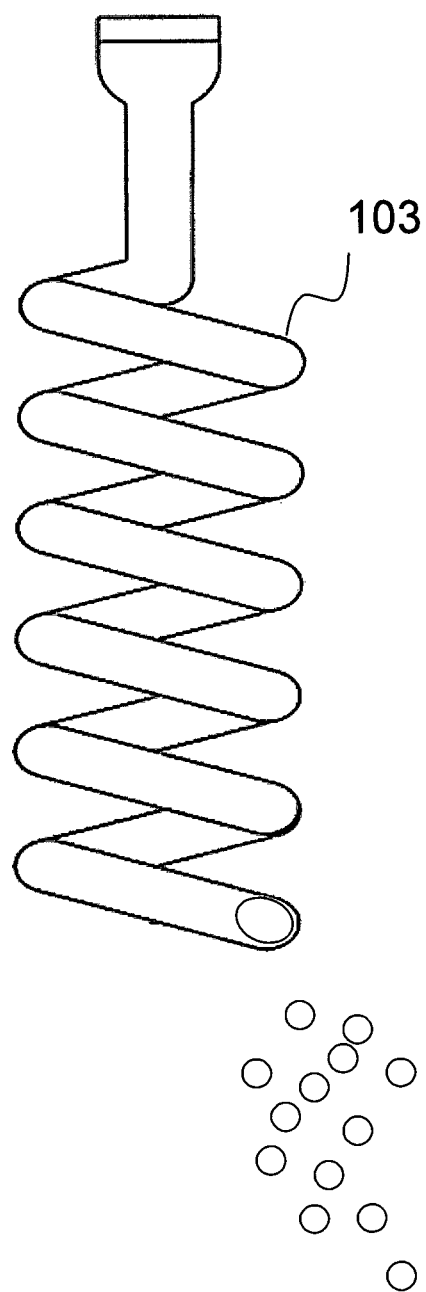
Figures 6A, 6B:
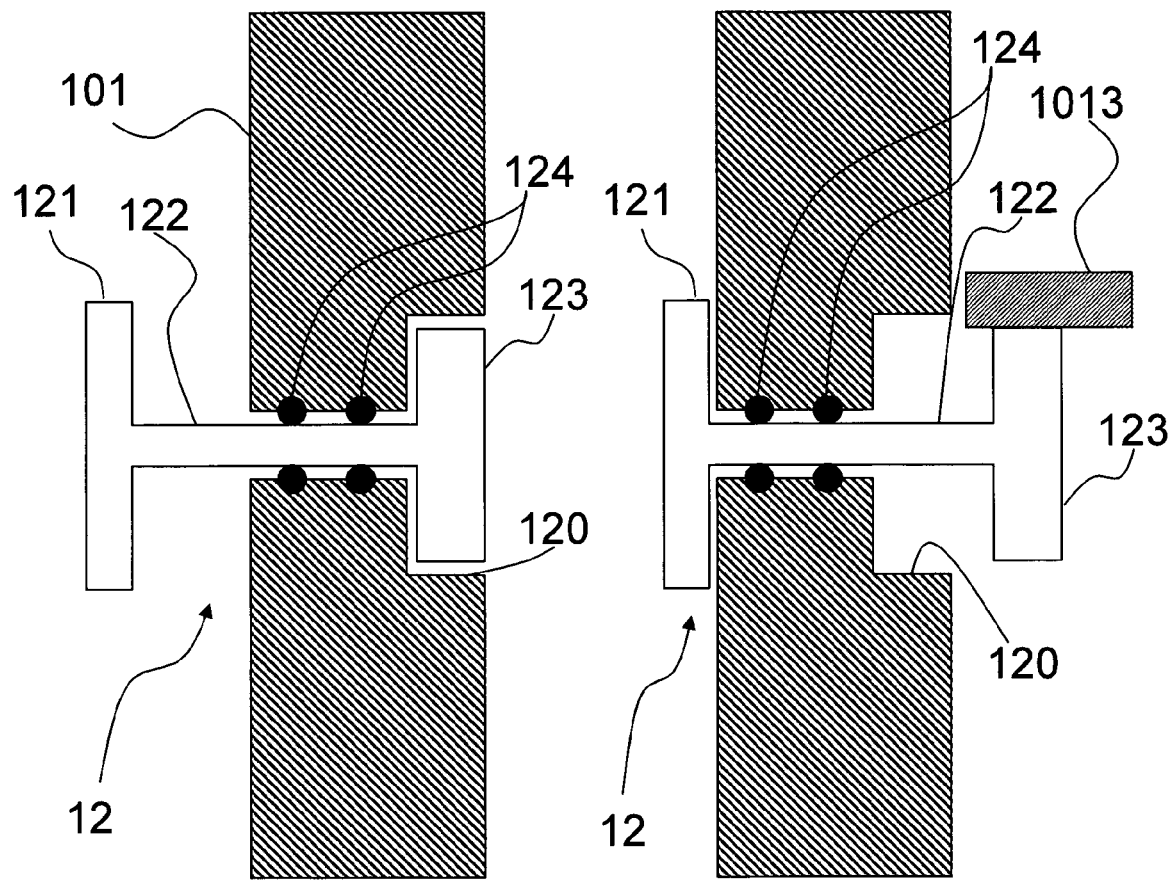

These and other features and advantages of the present invention will appear more clearly from the following description of a few embodiments, illustrated in the annexed drawings, in which:

FIG. 1 shows a first part of the fat treatment device that allows separation and size reduction of the suctioned lobular fat, FIGS. 1a, 1b, 1c show variants of the means for obtaining separation and size reduction of the suctioned lobular adipose tissue, FIG. 2a shows a second part of the fat treatment device that allows separation of the cell suspension from the liquid phase, FIG. 2b is a cross section of the second part of the device, FIG. 3 is a schematic view of the device of the present invention, which is composed of a first part for separating and reducing the size of the lobular adipose tissue and a second part for washing and separating the solid cell phase from the liquid phase, said two parts being removably connected, FIGS. 4a, 4b, 4c, 4d are schematic views of the steps for treatment of the liposuctioned lobular adipose tissue by the device of the present invention, FIG. 5 shows a needle or cannula for injecting the fat material treated according to the present invention, FIGS. 6a and 6b show the idle and operating states of an embodiment of the means for supporting said lobular fat reducing means.

The device of the present invention provides a cell suspension of adipose tissue to be used as a biological filler, i.e. a filler of natural and autologous origin, during body and face volume correction procedures and/or during biological stimulation of any tissue or organ injected with said treated adipose material.

The lobular fat material, i.e. the macroagglomerates of cells, particularly adipocytes, that are treated by the device of the present invention, may be obtained by means of a liposuction procedure which involves extraction of adipose tissue from donor areas of the patient, e.g. subcutaneous hip, abdomen or knee areas, under local anesthesia or generally in outpatient settings.

Once said adipose tissue has been treated with the device of the present invention, it can be used for autotransplantation, i.e. injection into special areas of the body of the patient from which the tissue has been withdrawn, to fill areas that, due to aging, diseases or past surgery, exhibit volume deficiencies or reabsorption of subcutaneous fat, with the relevant part of the body being sunken, with projecting bones and sagging skin.

The liposuction procedure is carried out as is known in the art.

The device and method as described and claimed below use the suctioned lobular fat to obtain a cell suspension with a solid phase consisting of cells, cell agglomerates having small and averagely constant sizes, and a liquid phase free from any impurity such as blood, oil, cell debris and anesthetic liquid.

As shown in FIG. 1, the device 1 of the present invention has at least one first part 101, consisting of a sterile container with an inner chamber divided into at least two portions, particularly a first upper portion 1011 and a second lower portion 1012, size reducing means 1013 for reducing the size of the lobular fat yielded by liposuction into cells and agglomerates of cells, particularly adipocytes and stem cells, of small and identical or similar sizes.

Said size reducing means 1013 consist of at least one net of intersecting wires or blades made of a sterile material, e.g. sterilized metal, acting as a cutting net subtended within the container 101, and oriented substantially perpendicular to the flow of fat into said container 101, into which the liposuctioned fat is injected or poured.

Otherwise, said size reducing means 1013 may consist of a series of sharp blades.

Said container 101 may be formed as a 3 cm diameter cylinder or like a syringe barrel.

Said container 101 has at least one inlet 104 for the fat material, possibly mixed with a sterile liquid, at the upper portion 1011, with reference to the fat flow therein, and at least one outlet 1015 in the lower portion 1012 of the chamber of the container 101, for the discharge of agglomerates of cells, particularly adipocytes, of small and averagely equal sizes.

Said at least one inlet 1014 and outlet 1015 may be closed with sterile caps and/or used in combination with backflow preventing means, such as one-way valves.

In a preferred embodiment, the fat material is injected into a feed line located on the sidewall of the cylinder, which is directly connected through a luer connector (luer connectors are sold, for instance, by GVS at www.gvs.com).

In a further variant, the cylindrical container may have a hollow-rod piston instead of the feed line, which is connected at one end, e.g. through a luer connector, to the tip of the drawing syringe, to allow adipose tissue to be transferred into the container without contacting the external environment.

Size reduction and standardization of cell agglomerates is obtained by the meshes of the net 1013 in the container 101, which net 1013 has meshes or flow-through interstices of identical sizes, with a diameter ranging from 0.01 mm to 2 mm, preferably from 0.5 to 1.5 mm, especially about 1 mm.

In a preferred embodiment, the interstices of the size reducing means for reducing the size of cell agglomerates have a 750 μm diameter. The diameter may be also smaller, provided it allows cell material to flow therethrough.

As lobular fat is poured or injected into the container 1, it is forced through the net 1013 or anyway through the macroagglomerate size reducing means, to come out of the outlet 1015 in the second lower portion 1012 of the container 101, using compression means, such as a syringe plunger or the like, which plunger is introduced through the upper base of the cylinder, which may coincide with the fat inlet, and is caused to tightly slide in said cylindrical container 101. By pressing the plunger, a pressure can be exerted in the container, with the fat material being forced at least once through the fat size reducing means 1013, so that cell agglomerates of reduced and averagely uniform sizes may gather in the lower portion 1012 of the chamber of the container 101.

Obviously, the flow of fat material through the meshes of the cutting net 1013 may be facilitated by mixing said fat material with liquids, particularly a saline.

In a further embodiment, two or more nets of wires or sharp blades 1013 may be provided in parallel arrangement in the container 101, and spaced from each other to divide the inner chamber of the container 101 into multiple portions.

Each of the nets 1013 subtended in the container 101 may have interstices or meshes of different sizes, particularly interstices with decreasing sizes from the net 1013 closer to the inlet 1014 to the net located at the outlet 1015 for fat agglomerates, so that size reduction of cell agglomerates a size equal to or smaller than a given value occurs in multiple steps through the nets 1013 in said container 101.

In a preferred embodiment, the discharge of reduced-size fat from said container 101 is facilitated by providing movable size reducing means 1013 in said container 101, that can be moved to the lower portion of the cylinder, next to the outlet.

FIGS. 6a and 6b are sectional views along a plane that passes through the longitudinal axis of the cylindrical chamber, of the idle and operating states of an embodiment of support means 12 for said lobular fat reducing means 1013, which allow movement thereof when they are retracted outwards.

By externally operating on the outer part 121, the through support element may be moved from an idle position, as shown in FIG. 6a, to an operating position, as shown in FIG. 6b and vice versa.

In the idle position, the inner part 123 is entirely held within said recess 120, whereas in the operating position the inner part projects into the cylindrical chambers and provides support to the size reducing means 1013.

In order to keep the internal environment of the container 101 isolated from the external environment, one or more seals or o-rings 124 are provided in the through hole, around the through rod 122.

Removable support means may be provided for supporting the size reducing means in the container.

Particularly, radial means may be provided, which are adapted to move from an innermost radial position to an outermost position, and in the innermost radial position said means act as supports for the size reducing means, whereas in the outermost radial position they leave said size reducing means free, particularly said size reducing means 1013 are free to slide in the second part 1012 of said chamber of the container 101, towards the outlet, said radial means being movable by electromagnetic means.

Therefore, with the presence of said support elements, once the fat has been reduced in size by being pressed against the net by the action of the plunger, the support means are disengaged, so that the net can fall toward the bottom of the cylinder 101 and allow the plunger to continue its stroke in the cylindrical chamber.

Thus, the adipose tissue, consisting of cell fragments, cells and cell agglomerates smaller than the liposuctioned macro-agglomerates may flow into the separation and washing container 102.

As shown in FIG. 2a, the device 1 of the present invention has, instead of or preferably in combination with the above container 101, at least one second part 102 consisting of a container for washing and separating the solid cell phase, represented by agglomerates of cells, particularly adipocytes and stem cells, from at least part of the liquid phase, consisting of an oily component, a blood component, preferably sterile solutions such as an anesthetic liquid and/or a saline and cell fragments.

As shown in FIG. 2a, said washing and separation container 102 may be in the form of a syringe and comprises at least two coaxial and concentric cylindrical chambers 1021, 1022, with the second chamber 1022 external to the first chamber 1021, the first inner chamber 1021 having at least one inlet 1023 for the liposuctioned material possibly mixed with a predetermined amount of liquid, e.g. saline, and at least one outlet 1024 for cell agglomerates, and the second outer chamber 1022 having at least one outlet 1025 independent from the first outlet 1024 for the discharge of at least part of the fluid phase, and the two chambers 1021, 1022 being also separated by a partition wall 1026 consisting of a selectively permeable membrane, that can retain cell agglomerates, individual cells and possibly cell fragments, and allow the flow of a mixture of fluid materials.

In one embodiment, said container 102, as shown in the figures, may be equipped with a plunger 108 sliding in said first chamber 1021, whose rod 1028 sealingly slides through the inlet 1023 so that said plunger 108 is sealingly slideable relative to both cylindrical chambers 1021, 1022 of the container 102.

Means may be provided at said inlet 1023, for ensuring that said rod of the plunger 108 and the container 102 slide relative to each other, such as two or more o-rings or the like.

Obviously, said inlet 1023 and said outlets 1025 and 1024 may be designed to be closed with sterile caps and/or be equipped with backflow preventing means, such as one-way valves, during separation and washing.

With said partition wall 1026, when the fat material, particularly cell agglomerates of small and averagely standardized sizes, mixed with a liquid material, such as saline, is introduced into the first inner chamber 1021 and pressurized by the compression means 108, said selectively permeable membrane 1026 allows the fluid materials to flow into the second outer chamber 1022 and retains said cell agglomerates, the cells and any cell fragments in the first inner chamber 1021.

Said selectively permeable membrane 1026 may consist of a net of fine meshes, which is smooth, i.e. with no projecting parts or irregular or sharp surfaces that might damage cell walls, whose meshes or through interstices are smaller than the cell agglomerates that come into and out of said washing and separation container 102, particularly said meshes have a diameter ranging from 0.01 mm to 1 mm, preferably from 0.1 mm to 0.5 mm, especially about 0.2 mm and possibly also about 250 μm.

In a further embodiment, the net that forms the partition wall 1026 between the two cylinders 1021, 1022 may be designed to have meshes of different sizes, e.g. the sizes of the meshes, i.e. the interstices that allow the liquid phase to flow out toward the second outermost cylindrical chamber 1022 may change according to the distance of said meshes from the fat inlet point 1023 in the first inner chamber 1021 while remaining in the above mentioned ranges of values.

According to a further variant, the partition wall 1026 may consist of multiple nets, with meshes that may possibly have different sizes, both within the same net and between adjacent nets, located in mutually facing positions, in adhering or spaced relation, to allow separation of two or more concentric cylindrical chambers.

The liquid waste phase flows through the selectively permeable membrane 1026 into the outermost cylindrical chamber 1022 from which it may come out through at least one outlet 1025, preferably located at the base of the cylinder or the shell, at the lower portion of the container 102, to be eliminated or separated from cell agglomerates.

Both the inlet 1023 and the outlets 1024 and 1025 may be equipped, at the outer surfaces of the container 102, with means for removable connection with other devices, which means may consist of snap or screw connection means, such as luer connectors or the like. According to the present invention, the outlet 1024 of the first inner chamber 1021 may be designed to be connected to a container for collection or storage of cell agglomerates, such as a syringe that may be used for transplantation of the treated adipose tissue into the above device 1.

In a further variant, the outlet 1024 of the first inner chamber 1021 may be designed to be connected to a second washing and separation container 102 or be directly connected to a cannula or an injection needle.

In one embodiment, the inlet 1023 of the inner chamber 1021 for introduction of the liposuctioned material is adapted to be connected with the outlet 1015 of the size reducing container 101, by means of a syringe, a cannula or the like with a connection line.

These connection means allow removable and sealing connection of the container 101 equipped with size reducing means 1013 for reducing the size of the lobular fat yielded by liposuction, directly to the container 102 for separating and washing the cell agglomerates from the liquid phase containing blood, sterile solutions such as saline and/or anesthetic solution and oil. By exerting pressure through the inlet 1014 in the upper portion of the container 101, with a syringe plunger, the lobular fat may be first pushed into the container 101 equipped with size reducing means to obtain cell agglomerates of smaller and constant sizes, or cell agglomerates whose sizes are equal to or smaller than a given value, and then into the inner chamber 1021 of the separation and washing container 102, in which said cell agglomerates are washed, e.g. by injecting and/or mixing the fat material with a saline, and separated from the liquid phase containing blood, oil and other waste products. The cell agglomerates so prepared, still due to the pressure exerted in the interconnected containers 101 and 102, may come out of at least one outlet 1024 formed in the inner chamber 1021 to be used during transplantation procedures, preferably autotransplantation of adipose tissue, whereas the liquid waste phase is caused to flow out separately from cell aggregates through the outlet 1025 of the outer chamber.

The outer end of the hollow rod 1028 may be designed to be hermetically sealed, or have one-way valves, to avoid undesired leakage of cell material when washing the cell aggregates in the first inner chambers 1021.

In the device 1 of the present invention, said at least one container 101 for reducing the sizes of cell aggregates to obtain cell aggregates of a size equal to or smaller than a given value and said at least one washing and separation container 102 for separating the cell aggregates from the liquid phase are connected in series in a removable fashion, so that they can be easily replaced, e.g. when they break or when the size reduction means 1013 for reducing the sizes of lobular fat obtained by liposuction or the selectively permeable membrane 1026 are clogged with said fat.

The cell material prepared using the device and method of the present invention may be injected into any type of tissue and with any suitable and known procedure.

Tunnels of very small diameters are formed in the tissues to facilitate integrations of the cells, and cell agglomerates in the interstitial spaces of the subcutaneous tissue or in the muscular tissue, thereby reducing surgical trauma and facilitating quick return to normal consistency of tissues undergoing volume increasing and remodeling treatments.

This optimizes tissue volume reconstruction and/or biological stimulation results. The reduction of fat lobule sizes by dividing such lobules into cell agglomerates affords a larger contact surface between the injected mass and the tissues being treated, thereby facilitating biological stimulation of the relevant areas and integration of the transplanted adipose tissue.

The use of particularly thin cannulae, ideally of less than 1 mm, is allowed by size reduction of liposuctioned lobular fat according to the invention. As an alternative to sterile cannulae with a blunted end, helical or spiral-shaped cannulae 103 having a pointed or blunted end like the one as shown in FIG. 5 may be used for transplantation of adipose cells.

Such type of cannula 103 also allows transplantation of cell agglomerates of high-consistency adipose tissues or particularly delicate tissues, such as dermis, scar tissue, bone, cartilage, myocardium or in other organs, through a single injection point that allows treatment of a certain volume of tissue. The cannula is introduced with a rotary motion to allow the helix to enter the tissue. Then, the cannula is extracted in the same manner while injecting cell agglomerates or clusters of adipose tissues. This will considerably increase the amount of transplanted adipose tissue per unit volume, as compared with individual injection by a rectilinear needle, and further increases the volume of treated volume without reducing the contact surface between the injected adipose tissue and the receiving tissue thereby increasing the vascularization potential of injected cells, as the adipose tissue is released as strips or very thin beads of cells, due to the small diameter of the cannula, and in a spiral path.

The use of these cannulae, that allow the prepared adipose tissue, containing, in addition to adipocytes, other types of cells including stem cells, to be released in a spiral path into the tissues to be treated, is particularly suitable when there is no way to perform Coleman filling, i.e. to form a net of tunnels in the tissue to be treated due, for instance, to excessive consistency of the tissue to be treated, or when tissue trauma is undesired, such as in myocardium treatment.

The spiral cannula affords a gentler introduction of the tissue into the area to be treated and a larger contact surface between the injected material and the area to be treated, for enhanced synergy between injected cells and receiving tissue.

The present invention also relates to a fat tissue for autotransplantation, which is composed of cells, possibly cell fragments and/or cell agglomerates, particularly adipocytes and stem cells of uniform size, with average diameters falling in the range from 0.01 mm to 2 mm, preferably from 0.25 to 1.5 mm, and especially being about 0.75 mm.

After preparation, this fat tissue has a very small liquid fraction, free of any impurity, which is mixed with cell agglomerates and is sufficient to facilitate introduction of the cells into the tissues to be treated.

Said liquid fraction may be less than 2% by weight of the adipose tissue prepared for transplantation.

The present invention also relates to a preferably sterile and disposable kit, containing:
- at least one container 101 having size reducing means 1013 for reducing the size of lobular fat, i.e. cell magroagglomerates, obtained by liposuction, into agglomerates of cells, particularly adipocytes and stem cells, of smaller and identical or similar sizes,
- at least one washing and separation container 102 for separating the solid cell phase represented by agglomerates of cells, particularly adipocytes and stem cells, from at least part of the liquid phase, consisting of an oily component, a blood component, preferably sterile solutions such as anesthetic liquid and/or saline and cell fragments.

The kit of the present invention may also include, alternatively or in combination:
- one or more disposable sterile syringes with different volumes,
- one or more sterile pointed needles or sterile lanceolate blades of different particular sizes to allow transcutaneous introduction of cannulae for anaesthesia, removal and transplantation,
- one or more disposable sterile cannulae having a pointed or blunted end, at least one of which has a very small diameter, of the order of 1 mm.

Instead of or in addition to said small diameter cannulae, the kit may include at least one helical or spiral-shaped cannula 103 with a pointed or blunted end, like the one shown in FIG. 5, allowing, as described above, transplantation of the cell mass of adipose tissue into high-consistency or particularly delicate tissues by increasing the volume of treated tissue with a single injection point.

The kit may also include an instrument for locking syringes during suction to temporarily prevent the plunger from bouncing back, e.g. during liposuction, and allow less traumatic adipose tissue suction.

The syringes in the kit may be made of plastic, preferably with a luer connector, or the like, and have various volumes. The following may be used, by way of example:
- 10 to 60 cc syringes for local anesthesia injection,
- 5 cc syringes with needle for creating a pomphus of anesthetic,
- 10 cc or larger volume syringes, connected to sterile 1.5 to 3 mm diameter cannulae for drawing adipose tissue from donor areas,
- 1 cc syringes for tissue transplantation.

Therefore, the treating method that may be carried out with the device of the present invention allows preparation of an adipose extract, e.g. obtained by liposuction, which is in the form of a mixture of fluid materials and cell fragments and one or more cell macroagglomerates of heterogeneous sizes, in a cell suspension containing cell agglomerates, particularly adipocyte agglomerates, with smaller and identical or similar sizes, in any case, smaller than a given value, to allow transplantation, or preferably autotransplantation into areas of the face or body of the patient, requiring a filling procedure with minor trauma, and accompanied by biological stimulation of the tissues involved in the procedure.

Obviously, the adipose tissue to be transplanted may be obtained not only by liposuction but also using other known techniques.

As described above, the sizes of cell agglomerates so obtained range from 0.01 mm to 2 mm, preferably from 0.25 to 1.5 mm, and are especially about 0.75 mm.

For instance, agglomerates may be obtained with an average size of 500 μm, or smaller, depending on the sizes of the meshes of the net that was used for liposuctioned material size reduction.

Therefore, the preparation of fat material involves the division of said fat material into cell fragments, cells or cell agglomerates that are smaller than the suctioned macroagglomerates.

The cell agglomerates so obtained undergo an additional treatment, which involves washing with sterile solutions and separation of the cell component from the liquid phases, i.e. blood, oil that comes out of the break of adipocytes, any anesthetic solutions in use, a solution, e.g. an impure saline.

Washing of cell agglomerates may continue until the liquid waste phase is perfectly clear.

Advantageously, cell agglomerates are washed after separation of lobules and macroagglomerates of adipose tissue and size reduction of said agglomerates below a predetermined value.

Adipose tissue washing is an important step, as it allows removal of cell fragments and oil resulting from the break of the cell walls of adipocytes during mechanical drawing of adipose tissue from donor areas and during size reduction of suctioned agglomerates.

The treating method implemented by the device 1 does not involve the use of enzymes or other components that can biologically activate agglomerate composing cells, but uses the possibility of changing the size of cell agglomerates, to obtain a larger exposed cell surface, that may contact the tissues treated during transplantation.

The device, kit and method as disclosed above, which form the subject of the present invention, may be obviously used not only for preparing adipose tissue to be transplanted, but also for preparing any type of cell agglomerate that is required to have a high purity level for use.

The invention claimed is:

1. A device for preparing adipose tissue for transplantation, said adipose tissue being obtained from lobular fat material extracted by liposuction, said fat material comprising a mixture of fluid materials and cell fragments, cells and one or more cell magroagglomerates of heterogenous sizes, comprising:
　at least one sterile size reducing container having a size reducing device configured to reduce a fat material into cell agglomerates of smaller and identical or similar sizes;
　an inner chamber defined within said container, wherein said size reducing device divides said inner chamber into at least two portions, said at least two portions comprising a first upper portion and a second lower portion; and
　a removable support device provided for supporting said size reducing device in said inner chamber, said support device being configured to be moved from a radially innermost position to a radially outermost position, such that, in the radially innermost position, said support device acts as a support for the size reducing device, whereas in the radially outermost position said support device leaves the size reducing device free to slide in the lower portion of the inner chamber of the size reducing container.

2. A device for preparing adipose tissue for transplantation, said adipose tissue being obtained from lobular fat material extracted by liposuction, said fat material comprising a mixture of fluid materials and cell fragments, cells and one or more cell magroagglomerates of heterogenous sizes, comprising:
　at least one sterile size reducing container having a size reducing device configured to reduce a fat material into cell agglomerates of smaller and identical or similar sizes;
　an inner chamber defined within said container, wherein said size reducing device divides said inner chamber into at least two portions, said at least two portions comprising a first upper portion and a second lower portion; and
　a sterile washing and separation container configured to separate a solid cell phase represented by agglomerates of cells, from at least part of a liquid phase comprising an oily component and a blood component, said washing and separation container being adapted to be removably connected to said size reducing container,
　wherein said washing and separation container comprises at least two chambers, a first and a second chambers, which are adjacent and separated by a partition element comprising a selectively permeable membrane, said selectively permeable membrane being adapted to retain a cell component and allow a mixture of fluid materials to flow therethrough, said first and second chambers having separate outlets, one of said chambers being designed to receive the cell component comprising cell fragments, cells and cell agglomerates, whereas the other one of said chambers is designed to receive a mixture of liquid materials, a device being provided exerting pressure and suction such to cause a mixture of fluid materials to flow from the first to the second chambers and vice versa through said selectively permeable membrane.

3. A device for preparing adipose tissue for transplantation, said adipose tissue being obtained from lobular fat material extracted by liposuction, said fat material comprising a mixture of fluid materials and cell fragments, cells and one or more cell magroagglomerates of heterogenous sizes, comprising:
　at least one sterile size reducing container having a size reducing device configured to reduce a fat material into cell agglomerates of smaller and identical or similar sizes;
　an inner chamber defined within said container, wherein said size reducing device divides said inner chamber into at least two portions, said at least two portions comprising a first upper portion and a second lower portion; and
　a sterile washing and separation container configured to separate a solid cell phase represented by agglomerates of cells, from at least part of a liquid phase comprising an oily component and a blood component, said washing and separation container being adapted to be removably connected to said size reducing container,
　wherein said washing and separation container is in form of a syringe and comprises at least a first and a second coaxial and concentric cylindrical chambers, the second chamber being external to the first chamber, the first chamber having at least one inlet for fat material, and at least one outlet for cell agglomerates, and the second chamber having at least one outlet independent from the outlet of the first chamber to discharge of at least part of a fluid phase, said first and second chambers being separated by a partition wall comprising a selectively permeable membrane configured to retain cell agglomerates, and allow a mixture of fluid materials to flow therethrough, a plunger being provided, sliding in said first chamber and having a rod that sealingly slides through the inlet of said first chamber so that said plunger is sealingly slideable relative to said first and second cylindrical chambers of the washing and separation container.

4. The device as claimed in claim 3, wherein the rod of the plunger is hollow with such an inside diameter as to allow small cell agglomerates to flow therein, and has an end adapted to be removably and sealingly connected with at least one outlet located in the lower portion of the size reducing container.

5. The device as claimed in claim 3, wherein said selectively permeable membrane comprises of at least one fine mesh net free of any ridges and surfaces shaped to damage cell walls, said at least one fine mesh being smaller than said cell agglomerates that come into and out of the inner chamber of said washing and separation container.

6. The device as claimed in claim 5, wherein said at least one fine mesh of the net has openings with sizes from 0.01 mm to 1 mm.

7. The device as claimed in claim 3, wherein the inlet of the first chamber is adapted to be removably and sealingly connected with a compression device, or to the outlet of said size reducing container, for reducing sizes of cell agglomerates, whereas the outlet of the first chamber or the outlet of the second chamber are adapted to be connected to a collection or storage container, to compression means, or directly to a cannula or an injection needle or an additional washing and separation container.

8. A device for preparing adipose tissue for transplantation, said adipose tissue being obtained from lobular fat material extracted by liposuction, said fat material comprising a mixture of fluid materials and cell fragments, cells and one or more cell magroagglomerates of heterogenous sizes, comprising:

at least one sterile size reducing container having a size reducing device configured to reduce a fat material into cell agglomerates of smaller and identical or similar sizes; and an inner chamber defined within said container, wherein said size reducing device divides said inner chamber into at least two portions, said at least two portions comprising a first upper portion and a second lower portion;

a sterile washing and separation container configured to separate a solid cell phase represented by agglomerates of cells, from at least part of a liquid phase comprising an oily component and a blood component, said washing and separation container being adapted to be removably connected to said size reducing container, wherein said device is comprised in a kit for preparing adipose tissue for transplantation from lobular fat extracted by liposuction, comprising:

said container having said size reducing device configured to reduce size of lobular fat obtained by liposuction into agglomerates of cells, said cells having sizes are below a given value; and said washing and separation container for separating a solid cell phase represented by cell agglomerates, cell and cell fragments, from at least part of a liquid phase comprising an oily component and a blood component, further comprising, alternatively or in combination:

one or more disposable sterile syringes with different volumes;

one or more sterile pointed needles or sterile lanceolate blades of different particular sizes to allow transcutaneous introduction of cannulae for anaesthesia, removal and transplantation;

one or more disposable sterile cannulae having a pointed or blunted end, at least one of said cannulae having a very small diameter of about 1 mm; and an instrument locking the syringes during suction to temporarily prevent a syringe piston from bouncing back and allow gradual non-traumatic suction of tissues.

9. The device as claimed in claim 8, wherein a helical or spiral-shaped cannula with a pointed or blunted tip is provided instead of or in addition to said cannulae.

* * * * *